United States Patent [19]

Budoff

[11] 4,405,321
[45] Sep. 20, 1983

[54] DOUCHE DELIVERY DEVICE

[76] Inventor: Penny W. Budoff, 11 Fairbankd Blvd., Woodbury, N.Y. 11797

[21] Appl. No.: 352,805

[22] Filed: Feb. 26, 1982

[51] Int. Cl.³ .............................................. A61M 1/00
[52] U.S. Cl. .................................................. 604/212
[58] Field of Search ...................... 128/232, 251, 225; 604/212, 187

[56] References Cited

U.S. PATENT DOCUMENTS

| 1,762,430 | 6/1930 | Tokita | 128/232 |
| 1,903,681 | 4/1933 | Merliss | 128/232 |
| 2,948,279 | 8/1960 | Mann | 128/232 |
| 3,474,788 | 10/1969 | Corbin et al. | 128/232 X |

FOREIGN PATENT DOCUMENTS 20458 of 1897 United Kingdom ................ 128/232

Primary Examiner—John D. Yasko
Attorney, Agent, or Firm—Darby & Darby

[57] ABSTRACT

This invention related to a disposable douche delivery device capable of use while seated as on a commode. The device includes preferably an outer container, in the shape of an open cage-like bulb arrangement, a disposable douche preparation container placed inside the outer container and capable of containing an effective quantity of douche preparation, a flexible retainer secured to the outer container within the outer container, and an arcuately shaped nozzle, formed with a valve, which nozzle is securable to the retainer.

14 Claims, 3 Drawing Figures

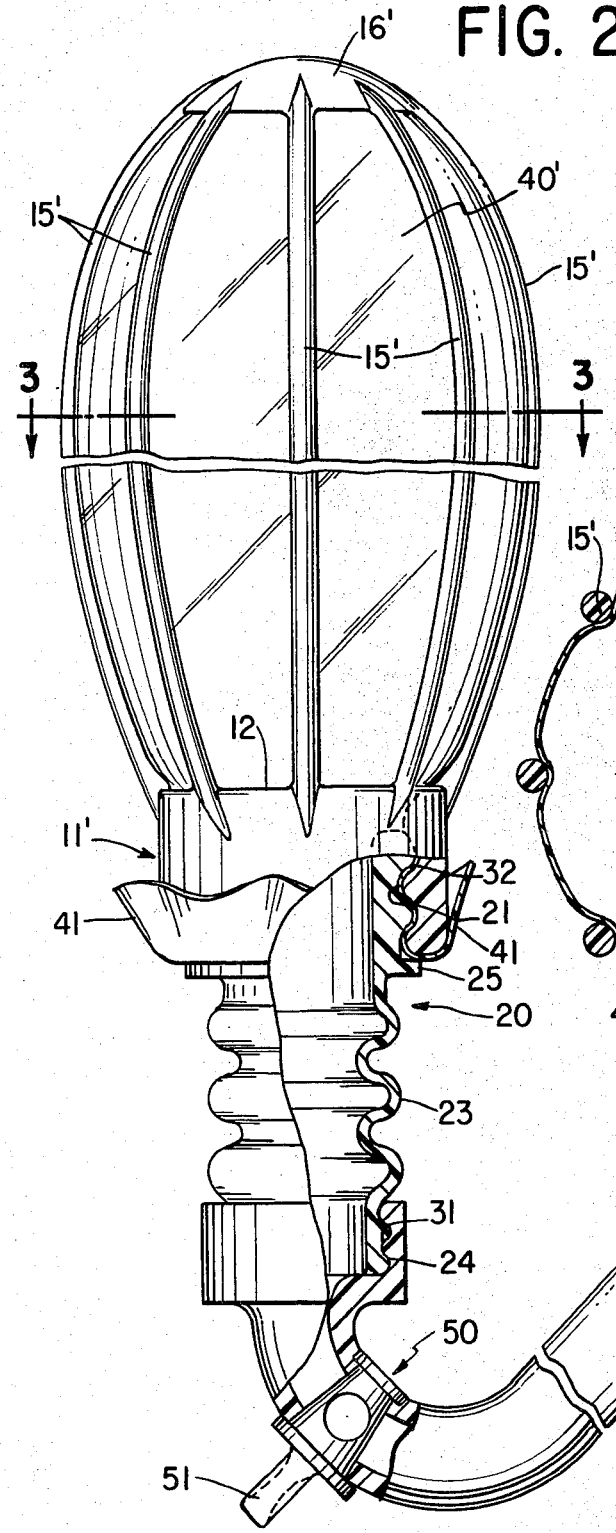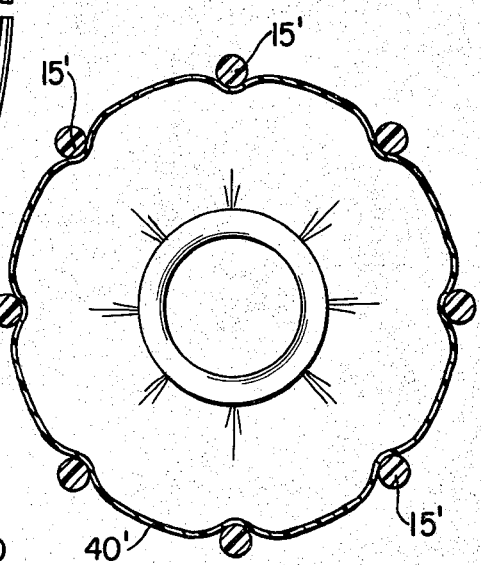

DOUCHE DELIVERY DEVICE

This invention relates to an improved douche delivery device and more particularly to a douche delivery device containing a disposable douche preparation container, and an arcuately shaped nozzle such that the device is capable of use while seated.

BACKGROUND OF THE INVENTION

The greatest benefit of douching is the mechanical cleansing that it provides. Although approximately one half of all women in this country douche, presently available douche preparations and douche delivery devices are either ineffective, inconvenient, time consuming or dangerous to use.

Conventional douche delivery devices contain a bag to hold the water and douche preparation and a substantially straight nozzle for insertion into the vagina. That nozzle is often connected directly to the bag as by providing the nozzle and the bag with complementary threaded portions for screw-attachment. Some douche delivery devices also contain a hose and valve arrangement so that the device can also be used as an enema bag.

In operating conventional douche delivery devices the user is required to lie on her back in a bathtub, manipulate the nozzle into her vagina and introduce the douche preparation into the vagina by repeated squeezing of the bag. After the douche preparation is so administered, the woman stands in the bathtub and allows the douche preparation and accumulated debris to slowly drain, by gravity, down her legs. This slow drainage has been found to be disadvantageous since accumulated debris is often left in the vaginal folds. This method for douching with conventional douche delivery devices is inconvenient and time consuming. In addition to the discomfort which the user must withstand, while lying on her back on a cold hard bathtub surface and manipulating the nozzle and the bag, the user must also spend considerable time after douching to cleanse her body of accumulated debris, infected water and the douche preparation which has trickled down her body.

Many conventional non-disposable douche bags are constructed of rubber and the douche preparation is administered directly from the rubber bag. These types of douche bags have been found to be dangerous. The interior of the rubber bag is damp and dark and serves as a culture media for the promotion and growth of bacteria. Pathogenic organisms cultured in the bag are transmitted into the woman's body upon subsequent douching and can lead to disease. In addition to this danger, inherent in non-disposable rubber douche bags, many conventional douche delivery devices do not empty completely or are very difficult to manipulate so as to empty completely. This increases their ineffectiveness and potential danger due to bacteria growth or from air being pumped into the vagina.

Furthermore even if a disposable douche preparation is used, that is, one with a removable container which is discarded after use, conventional douche delivery devices and douche preparations are not designed to provide a sufficient quantity of the douche preparation for adequate mechanical cleansing.

OBJECTS OF THE INVENTION

It is an object of the present invention to provide an improved, disposable douche delivery device which is effective for sanitary and fast mechanical cleansing while the user is seated avoiding the problems associated with prior art douche delivery devices.

A further object of this invention is to provide a douche delivery system with an improved nozzle for easy and comfortable insertion into the vagina.

A still further object of this invention is to provide a douche delivery device with an outer container and douche preparation container, or, alternatively, just the douche preparation container, containing a sufficient quantity of douche preparation for effective mechanical cleansing, which is easily manipulated and capable of being completely emptied.

SUMMARY OF THE INVENTION

In accordance with the invention, a douche delivery device comprises an outer flexible container, a retainer supporting the outer container and secured at a first end to the outer container, a disposable douche preparation container positioned substantially within the outer container and secured to the outer container by the retainer, and a nozzle having a valve, one end of the nozzle being attached to the second end of the retainer, the nozzle being shaped so as to allow easy insertion of the second end thereof into the vagina for douching while seated. Alternatively, the disposable douche preparation container may be self-supporting without the need for an outer container.

In a preferred embodiment of the invention the retainer is constructed of a flexible material and the nozzle is arcuately shaped such that the second end of the nozzle, furthest from the retainer, is disposed in a direction such that the retainer and nozzle are easily manipulated for use in a seated position.

In the preferred embodiment of the invention the outer container and disposable douche preparation container are capable of holding, and completely administering, at least one liter of the douche preparation into the vagina.

BRIEF DESCRIPTION OF THE DRAWINGS

FIG. 2 is an elevation view in partial cross-section of the douche delivery device of the invention containing an alternately formed outer container.

FIG. 3 is a section view taken along the line 2—2 of FIG. 2.

DETAILED DESCRIPTION OF A PREFERRED EMBODIMENT

Figure 1:
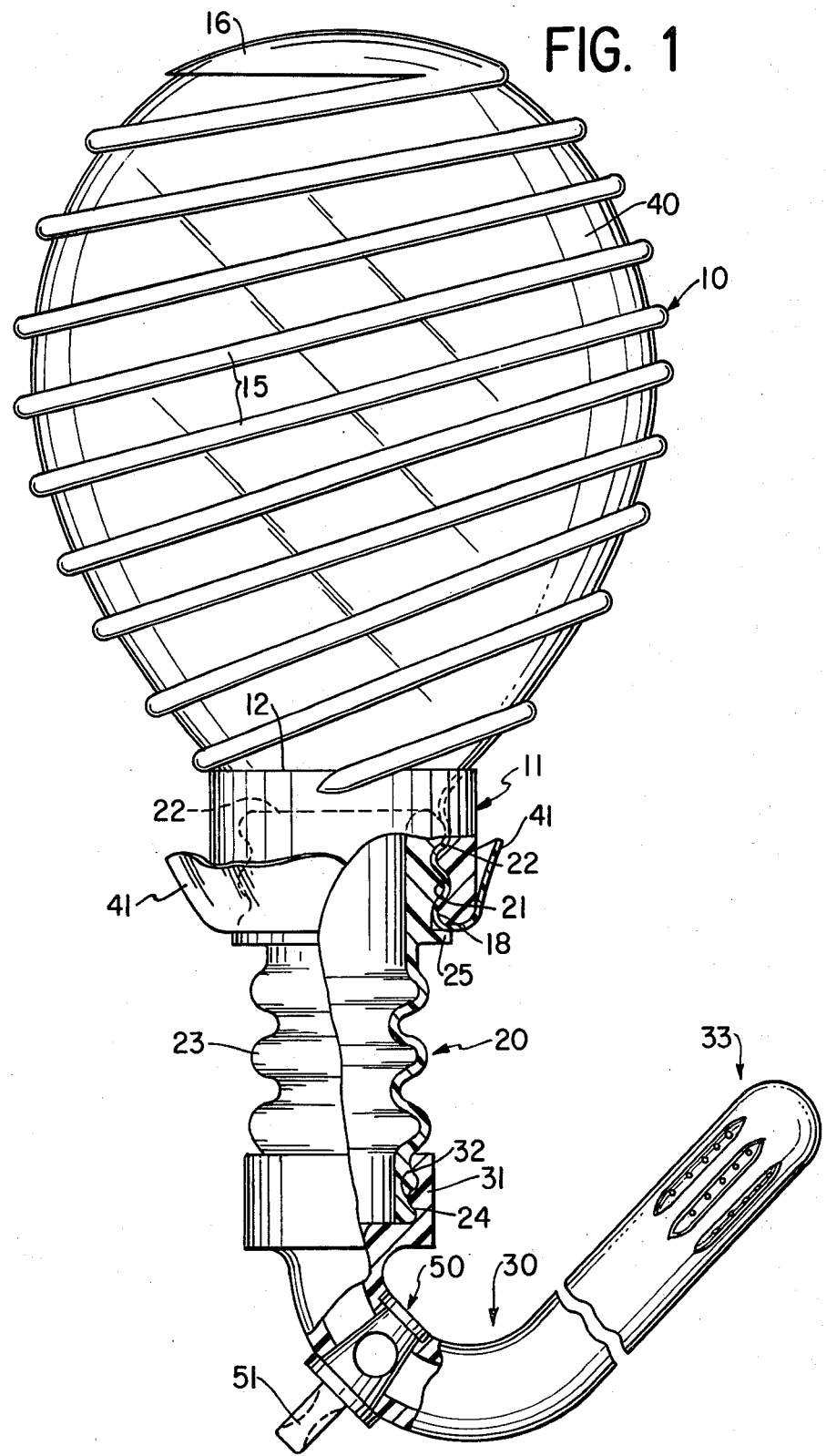
FIG. 1 is an elevation view in partial cross-section of the preferred douche delivery device of the invention.

Referring to FIG. 1, a preferred embodiment of the douche delivery of the present invention contains an outer container 10, a retainer 20 and a nozzle 30. The disposable douche preparation container 40 is shown, positioned substantially within outer container 10. Outer container 10 is preferably in the shape of a bulb with a cylindrical collar 11 surrounding the opening formed in the bottom 12 of the outer container 10. The outer container 10 is constructed of a resilient material, such as an elastomer or natural rubber, which is easily deformable upon the application of pressure and which regains and retains its original shape after the pressure is removed. The volume of the outer container 10 preferably must be sufficient to allow substantially one liter of a douche preparation to be placed inside a disposable douche preparation container 40 which, in turn, is placed substantially inside the outer container 10. The outer container 10 and collar 11 are preferably of an integral construction. However, it is possible to form them as separate parts which can be joined together. The outer container 10 is preferably constructed in an open cage-like arrangement with one or more ribs or bars 15 extending between the top 16 and collar 11 in a spiral or helix as shown in FIG. 1. The open cage-like arrangement may alternatively be formed by ribs 15', which extend vertically from top 16' to collar 11' as shown in FIGS. 2 and 3. When the outer container 10 is formed in an open cage-like arrangement, the user is able to determine the level of the douche preparation in douche preparation container 40. It is also possible to form ribs 15 as one or more separate pieces joined to each other and to the outer surface of a closed ribbed outer container 10. The ribs 15 allow the user to grasp and squeeze the outer container 10 at various points between the top 16 and the bottom 12 causing the entire douche preparation to be transmitted, by the decrease in the volume of outer container 10 and douche preparation container 40, into the vagina. Of course, the outer container 10 and the douche preparation container may be so constructed as to be one container which combines the features and functions of outer container 10 and douche preparation container 40.

The lower portion of the interior surface of collar 11, surrouding the opening formed in the bottom 12 of outer container 10, is constructed such that it may be joined in any suitable manner with the first or upper end 22 of the retainer 20. Preferably either the lower portion of the interior surface of collar 11 or the exterior surface of first end 22 of retainer 20 is formed with threads 21 while the other piece is formed with complementary ridges for screwing the collar onto the first end 22 of retainer 20.

Retainer 20 is attached to and supports the outer container 10. It is preferably formed with a midsection 23, between ends 22 and 25, constructed of a thin-walled flexible material such as an elastomer or rubber so that the midsection of the retainer may be bent to assist in positioning the nozzle 30 into the vagina. It is also possible to construct the entire retainer 20 of such a flexible material. The midsection 23 of retainer 20 is preferably formed with accordion-like projections to optimize the ease of manipulation and bending of the retainer 20. The interior surface of the second or lower end 25 of retainer 20 is preferably formed with threads 24 which mate with the threads 32 on the outer surface of the first end 31 of the nozzle 30 so that they may be joined together.

Nozzle 30 is a substantially hollow tube formed with a first end 31 and a preferably rounded and substantially closed second end 33. Nozzle 30 is preferably constructed of a relatively resilient material such as an elastomer or plastic. First end 31 is constructed so as to be attachable to and preferably detachable from the second end 25 of retainer 20 as described above. It is however, possible to form nozzle 30 as an integral piece with retainer 20. Preferably, nozzle 30 is detachable from retainer 20, in the same manner as the collar 11 is detachable from outer container 10, so that all the elements forming the device may be separately cleaned and conveniently stored together, as in a small case, when the device is not in use. First end 31 of nozzle 30 may be formed having an internal diameter larger than the internal diameter of the rest of the nozzle as shown in FIGS. 1 and 2. The first end 31 of the nozzle 30 is formed with a pair of aligned holes on opposite sides thereof. A cut-off valve 50 or stop cock is positioned within the aligned holes in nozzle 30. One end of valve 50 is formed with a handle 51 located on the outer surface of one side of the nozzle 30. While this valve 50 may be located at various points along the length of the nozzle 30, it is preferable to locate the valve 50 at a position closer to the first end 31 of nozzle 30 than to the second end 33, and more particularly on the nozzle 30 at a position substantially near to the second end 25 of retainer 20, so that the user may adjust the position of the retainer 20 and simultaneously actuate the valve 50 with one hand. Valve 50 mechanically controls the flow of the douche preparation into the vagina when the outer container 10 is squeezed. When the valve 50 is closed the douche preparation does not flow through the nozzle 30, and when the valve 50 is opened, to various positions, the rate of flow of the douche preparation into the vagina is controlled.

The curvature of the hollow nozzle 30, between ends 31 and 33, allows for the operation of the douche delivery device of the present invention, as it allows the device to be employed when the user is seated on a commode or toilet. The use of the present douche delivery device when the user is seated on a toilet prevents the discharge of the administered douche preparation and accumulated debris from slowly draining down the woman's legs. Accordingly, the time required to douche, in the seated position, is reduced over the time required to douche with conventional devices. The time required to thoroughly cleanse after douching is also reduced. The nozzle 30 is shaped so as to be compatible with the angle of the entrance to the vagina when the user is seated. This requires the arcuately curved nozzle to be curved in a direction upwards so as to be used by a woman in the seated position. The second end 33 of nozzle 30 is preferably disposed at an angle less than 90° to the axis of retainer 20. The smooth arcuately shaped nozzle allows end 33 of the nozzle 30 to be comfortably inserted into the vagina. End 33 of the nozzle 30 is preferably substantially closed and rounded as shown in FIGS. 1 and 2. End 33 of the nozzle 30 is preferably formed with a plurality of longitudinally disposed holes in series which extend into the hollow center of the nozzle, each set of the series being spaced apart from each adjacent set and all the sets extending around the outer surface near the second end 33 of nozzle 30. When end 33 of the nozzle 30 is inserted into the vagina, the holes formed near end 33 of the nozzle are thereby preferably positioned at an acute angle to the vagina to maximize the cleansing action. It is also possible to form the tip of the end 33 of nozzle 30 with holes such that the douche preparation can be injected directly into the vagina. The diameter of the holes formed in the nozzle is preferably smaller than the interior diameter of the hollow nozzle 30 such that the douche preparation is injected into the vagina in the form of a concentrated spray.

Douche preparation container 40 is disposable. This eliminates the possibility of bacterial growth as described above with reference to non-disposable douche delivery devices. The douche preparation container 40 should be fabricated of a flexible material, such as polyethylene or other synthetic or natural polymers known in the art, and must be capable of holding substantially one liter of douche preparation fluid. At least one liter of douche preparation is the preferred minimum required for adequate mechanical cleansing. The container 40 is also capable of administering less than one liter of douche preparation. The douche preparation container 40 may be fabricated of a transparent or transluscent material so that when outer container 10 is formed in an open cage-like arrangement, as described above, the user can see the level of the douche preparation inside the container 40. The douche preparation container 40 is placed within outer container 10 with the outer portion 41 of the douche preparation container 40 surrounding the opening of the outer container 10 and extending below and folded upwardly and about the bottom of the collar 11. The douche preparation container 40 is then secured within outer container 10 and to collar 11 when the retainer 20 is connected to the collar 11. The lower inner surface 18 of the collar 11 presses the douche preparation container 40 into contact with the first end 22 of the retainer 20. The outer portion of container 40 is preferably secured between mating threads 21 and 22 of the collar 11 and the retainer 20 respectively. The douche preparation is then added to the device by inverting the outer container 10 and pouring an effective quantity of douche preparation through the retainer 20 and into the douche preparation container 40. The nozzle 30 is then secured to the second end 25 of the retainer 20 and the valve 50 is placed in the closed position. When the outer container 10 is then inverted, to its original position, the douche preparation is located within the disposable douche preparation container 40, the retainer 20 and the first end 31 of nozzle 30 up to valve 50. The douche device is then in position for operation. By manipulating the retainer 20 and the second end 33 of the nozzle 30, the nozzle is inserted into the vagina of the seated user. By grasping and squeezing outer container 10 in one hand and by opening valve 50 and pressing the labia or vaginal lips against the nozzle 30 for a few seconds the douche preparation fills the vagina. When the vaginal lips are compressed the vaginal wall is adequately ballooned out for effective cleansing of and between the vaginal folds. Upon releasing the labia, the douche preparation and accumulated debris gushes directly into the toilet by the action of gravity without contacting other parts of the body. When the user is seated, as on the toilet, the slant of the entrance of the vagina and the force of gravity places the vagina in a much better position to quickly empty than when the user is standing. The rapid emptying of the filled vagina thus allows the douche preparation to more efficiently cleanse because it carries more debris and loosened sediment along with it than when the drainage is slower. Contrary to the slow draining of conventional douche delivery devices (with the user standing after application of the douche preparation), there is less time available with the douche delivery device of the present invention for infected material to settle out in the upper vagina. The entire douching process described above can be efficiently completed in a couple of minutes.

Upon completion of the operation, nozzle 30 is disconnected from retainer 20, and retainer 20 is disconnected from collar 11. The douche preparation container 40 is then removed and discarded and the nozzle, retainer and outer container may be cleaned, dried and stored for subsequent use.

In utilizing the disposable douche delivery device of the present invention the douche preparation should preferably contain lukewarm water and a natural douche preparation containing primarily lactic acid with no fragrances, dyes or iodine compounds. Detergents or wetting agents may be used in conjunction with diluted lactic acid in order to help emulsify vaginal secretions and liquefy small particulate matter so that the douche solution can carry it all away.

While a preferred form of the invention has been illustrated and described, it will be apparent that various changes or modifications may be made without departing from the spirit and scope of the invention as sought to be defined in the claims.

What is claimed is:

1. A douche delivery device comprising:
   an outer container;
   a retainer secured at its upper end to the lower portion of said outer container, said retainer having an opening formed therein extending from the upper to the lower end of said retainer;
   a disposable douche preparation container positioned substantially within said outer container and secured thereto by said retainer; and
   a nozzle being hollow along its length and having a valve positioned along said nozzle, one end of the nozzle being secured to the lower end of said retainer, said nozzle being arcuately shaped so as to allow easy insertion of the second end of said nozzle into the vagina for douching while seated.

2. The douche delivery device according to claim 1 wherein the retainer is constructed of a flexible material.

3. The douche delivery device according to claim 1 wherein the disposable douche preparation container is flexible and capable of holding and completely administering an effective quantity of the douche preparation into the vagina.

4. The douche delivery device according to claim 1 wherein the outer container is formed as an open cage-like arrangement comprising a collar surrounding an opening formed at a first end and one or more ribs extending in a spiral direction from a second end to said first end.

5. The douche delivery device according to claim 1 wherein the outer container is formed in a closed ribbed arrangement with an outer surface having ribs extending in a spiral direction around said outer container such that said outer container can be grasped and squeezed at various points along its length.

6. The douche delivery device according to claim 3 wherein the disposable douche preparation container is formed of polyethylene and wherein the effective quantity of the douche preparation is substantially one liter.

7. The douche delivery device according to claim 1 wherein the nozzle includes a rounded, substantially closed second end formed with a plurality of longitudinally disposed holes in series positioned around the outer surface of said second end and extending into the hollow portion of the nozzle.

8. The douche delivery device according to claim 1 wherein said outer container, said retainer and said nozzle are adapted to be disconnected from one another so that they may be cleaned, dried, and stored.

9. The douche delivery device according to claim 1 wherein said retainer further comprises a flexible midsection capable of bending so as to facilitate insertion of the nozzle into the vagina.

10. The douche delivery device according to claim 4 wherein said valve is positioned in said nozzle at a point substantially adjacent to said lower end of said retainer such that the retainer and said valve may be simultaneously manipulated.

11. The douche delivery device according to claim 4 wherein the disposable douche preparation container is formed as a transparent or transluscent material such that the level of a douche preparation placed therein is visible to the user through the open cage-like outer container and disposable douche preparation container.

12. A douche delivery device comprising:
   a flexible, resilient outer container having a collar at its bottom surrounding an opening formed in the outer container,
   a flexible retainer secured at its upper end to the collar of the outer container;
   a disposable douche preparation container positioned substantially within the outer container and having its ends extending beneath and folded about said collar and being secured to said collar by said retainer;
   a hollow arcuately shaped nozzle having a valve located substantially at its first end for controlling the flow of a douche preparation, said first end being secured to the lower end of said retainer, said nozzle being arcuately shaped so as to allow easy insertion of the second end thereof into the vagina for douching while seated, said second end of said nozzle being rounded and substantially closed and being formed with a plurality of longitudinally disposed holes in series positioned around the outer surface of said second end and extending into the hollow portion of the nozzle, such that said douche preparation enters the vagina; and
   a natural douche preparation comprising water and lactic acid.

13. A method for douching while seated on a toilet utilizing the douche delivery device according to claim 1 and a natural douche preparation comprising water and lactic acid, comprising:
   inverting said outer container and connected douche preparation container and retainer;
   pouring an effective quantity of said douche preparation into said douche preparation container;
   securing one end of said nozzle to said retainer, with said valve in the closed position;
   inserting a second end of said nozzle into the vagina;
   opening said valve,
   applying pressure to the outer container to fill the vagina; and
   allowing said douche preparation to fill the vagina and allowing accumulated debris to rapidly exit from the vagina into the toilet by the operation of gravity.

14. The method according to claim 13 wherein said steps of opening said valve, applying pressure to the outer container allowing said douche preparation to fill the vagina and allowing accumulated debris to rapidly exit from the vagina into the toilet by operation of gravity, is repeated until the douche preparation container empties completely.

* * * * *